(12) United States Patent
Daxer (10) Patent No.: US 7,922,735 B2
(45) Date of Patent: Apr. 12, 2011

(54) DEVICE FOR CUTTING THE CORNEA OF AN EYE

(76) Inventor: Albert Daxer, Linz (AT)

( * ) Notice: Subject to any disclaimer, the term of this patent is extended or adjusted under 35 U.S.C. 154(b) by 0 days.

(21) Appl. No.: 10/555,353

(22) PCT Filed: Apr. 30, 2004

(86) PCT No.: PCT/AT2004/000147
§ 371 (c)(1),
(2), (4) Date: Sep. 29, 2006

(87) PCT Pub. No.: WO2004/096106
PCT Pub. Date: Nov. 11, 2004

(65) Prior Publication Data
US 2007/0016234 A1 Jan. 18, 2007

(30) Foreign Application Priority Data

May 2, 2003 (AT) .................................. A 663/2003
May 30, 2003 (AT) .................................. A 840/2003
Aug. 12, 2003 (AT) .................................. A 1264/2003
Feb. 25, 2004 (AT) .................................. A 299/2004

(51) Int. Cl.
*A61F 9/00* (2006.01)
(52) U.S. Cl. ........................................................ 606/166
(58) Field of Classification Search .................. 606/166, 606/161, 181, 171, 169, 170, 172, 167, 5, 606/4, 10, 107, 162, 168; 623/4.1–5.15
See application file for complete search history.

(56) References Cited

U.S. PATENT DOCUMENTS

| | | | | |
|---|---|---|---|---|
| 4,662,370 A | * | 5/1987 | Hoffmann et al. | 606/166 |
| 5,215,104 A | * | 6/1993 | Steinert | 128/898 |
| 5,342,378 A | * | 8/1994 | Giraud et al. | 606/166 |

(Continued)

FOREIGN PATENT DOCUMENTS

DE 34 33 581 A 3/1986

(Continued)

OTHER PUBLICATIONS

International Search Report.

(Continued)

*Primary Examiner* — (Jackie) Tan-Uyen T Ho
*Assistant Examiner* — Jocelin C Tanner
(74) *Attorney, Agent, or Firm* — Collard & Roe, P.C.

(57) ABSTRACT

The invention relates to a device for cutting the cornea of an eye to correct the refractive power thereof, having a frame that comprises a fixation ring, which may be drawn onto the eye, as well as a receptacle, which may be coaxially displaced relative to the fixation ring and which serves to accommodate an applanator for deforming the cornea within the fixation ring, and a holding device, which is guided on the frame in a plane that is perpendicular to the axis with regard to the fixation ring and which serves to hold a blade, which passes through the frame via a peripheral recess and which is mounted in front of the applanator, being radially displaceable relative to the fixation ring as well as movable around an axis perpendicular to the guiding plane, for the purpose of cutting a pocket through a merely tunnel-like entry into the corneal tissue. In order to obtain advantageous cutting conditions, it is suggested to have the blade pass through the frame recess with clearance, and to have the holding device support a vibrator for setting the blade in oscillatory motion in the cutting plane.

23 Claims, 6 Drawing Sheets

U.S. PATENT DOCUMENTS

| | | | |
|---|---|---|---|
| 5,549,632 A * | 8/1996 | Lai | 606/5 |
| 5,556,406 A | 9/1996 | Gordon et al. | |
| 5,624,456 A * | 4/1997 | Hellenkamp | 606/166 |
| 5,817,115 A * | 10/1998 | Nigam | 606/166 |
| 5,964,776 A * | 10/1999 | Peyman | 606/166 |
| 6,056,764 A * | 5/2000 | Smith | 606/167 |
| 6,083,236 A * | 7/2000 | Feingold | 606/166 |
| 6,126,668 A * | 10/2000 | Bair et al. | 606/166 |
| 6,132,446 A * | 10/2000 | Hellenkamp et al. | 606/166 |
| 6,139,559 A * | 10/2000 | Nordan et al. | 606/166 |
| 6,312,440 B1 * | 11/2001 | Hood et al. | 606/166 |
| 6,358,262 B1 * | 3/2002 | Chan et al. | 606/166 |
| 6,506,198 B1 | 1/2003 | Amano | |
| 6,615,496 B1 * | 9/2003 | Fleming et al. | 30/350 |
| 6,923,821 B2 * | 8/2005 | Wortrich | 606/166 |
| 2001/0004702 A1 | 6/2001 | Peyman | |
| 2004/0260320 A1 * | 12/2004 | Lisk et al. | 606/166 |

FOREIGN PATENT DOCUMENTS

| | | |
|---|---|---|
| DE | 34 33 581 A1 | 3/1986 |
| WO | WO 03/015674 | 2/2003 |

OTHER PUBLICATIONS

Daxer A. et al., "Collagen Fibrils in the Human Corneal Stroma: Structure and Aging," Invest. Opthalmol & Vis. Sci, Mar. 1998, vol. 39, No. 3, pp. 644-648.

Eisner, "Eye Surgery: An Introduction to Operative Technique" Springer-Verlag Berlin Heidelberg 1978, pp. 67-69.

* cited by examiner

DEVICE FOR CUTTING THE CORNEA OF AN EYE

CROSS REFERENCE TO RELATED APPLICATIONS

Applicant claims priority under 35 U.S.C. §119 of Austrian Patent Application Serial No. A663/2003 filed May 2, 2003, Austrian Patent Application Serial No. A840/2003 filed May 30, 2003, Austrian Patent Application Serial No. A1264/2003 filed Aug. 12, 2003 and Austrian Patent Application Serial No. A299/2004 filed Feb. 25, 2004. Applicant also claims priority under 35 U.S.C. §365 of PCT/AT2004/000147 filed Apr. 30, 2004. The international application under PCT article 21(2) was not published in English.

1. Field of the Invention

The invention relates to a device for cutting the cornea of an eye in order to correct the refractive power thereof, having a frame that comprises a fixation ring, which may be drawn onto the eye, as well as a receptacle, which may be coaxially displaced relative to the fixation ring and which serves to accommodate an applanator for deforming the cornea within the fixation ring, and a holding device, which is guided on the frame in a plane that is perpendicular to the axis with regard to the fixation ring and which serves to hold a blade that passes through the frame via a peripheral recess and is mounted in front of the applanator, being radially displaceable relative to the fixation ring as well as movable around an axis perpendicular to the guiding plane via the holding device, for the purpose of cutting a pocket through a merely tunnel-like entry into the corneal tissue.

2. Description of the Prior Art

In order to be able to correct the refractive power of the cornea of an eye, a known method (US 2001/0004702 A1) is to treat the interior of the corneal tissue via an entry that may, for example, be approximately 4 mm wide. This method serves to create a pocket inside the corneal tissue, into which an implant for refractive power correction may be inserted. In comparison to other methods for correcting the refractive power, where either the surface of the corneal tissue is ablated (DE 34 33 581 A1) or the cornea is broadly incised to produce a flap that may be folded back (LASIK method), treating the interior of the cornea via a tunnel-like entry has the advantage that postoperative pain and/or impairment of the stability of the cornea are kept to a minimum since the top layer essential for the stability of the cornea, which also includes the Bowman's membrane, remains largely uninjured.

Therefore, treating the cornea via a tunnel-like entry offers multiple advantages in relation to the other methods of treatment. In order to be able to perform such a refractive power correction, US 2001/0004702 A1 suggests attaching a frame to the eye of the patient on which a holding device for a movable blade is mounted. The blade passes through the frame via a peripheral recess and is guided in a guiding plane by means of a holding device. This guiding plane lies parallel to the cutting plane of the blade, a pocket being produced in the cornea in said cutting plane. The blade in its cutting plane is additionally held down by a spring so as to rest on the frame as slipping of the blade when being placed on the cornea for producing the tunnel-like entry must be avoided. That is to say, it is relatively difficult to penetrate the elastic and extremely tough outer layer of the cornea. Moreover, the blade must not get deformed during cutting as in that case an exact cutting plane and preventing perforation of the outer or inner layer of the cornea may not be guaranteed, whereby the successful correction of the refractive power would be precluded. While this eventuality may be counteracted by using blades of greater hardness (e.g. made of diamond material), such blades are particularly sensitive to shear stress, which excludes the use of said blades in the device according to US 2001/0004702, given the fact that the blade rests on the frame. Moreover, such blades bear the risk of breakage and also their sharpness would be greatly impaired.

Another known state-of-the-art method (LASIK, U.S. Pat. No. 5,556,406 A) consists in broadly incising the corneal tissue to produce a flap which is then folded back, and ablating a portion of the exposed corneal tissue by using a laser, or alternatively applying an artificial lens before placing the corneal flap back in its original position. This method has the disadvantage that, as already noted, the stability of the cornea is greatly impaired, which may occasionally result in undesirable bulges of the corneal surface.

SUMMARY OF THE INVENTION

The underlying objective of the present invention therefore is to design a device for cutting the cornea of an eye to correct its refractive power on the basis of the state-of-the-art technique initially described in such a way that, departing from the very point at which the tip of the blade is placed on the cornea, a pocket lying in the cutting plane of the blade may be cut via a tunnel-like entry, without any impairment of the stability of the cornea to be expected. In addition, the device shall be aimed at allowing a broad range of refractive power corrections.

The invention accomplishes the set objective in that the blade passes through the frame recess with clearance, and that the holding device supports a vibrator for setting the blade in oscillatory motion in the cutting plane. Having the blade pass through the frame recess with clearance ensures that the blade does not rest on the frame during displacement, particularly when introducing the blade into its cutting position, so that damage to the blade and/or the edge of the blade may be precluded. It is therefore possible to use comparatively hard materials for the blade since the brittleness of these usually very hard materials need not be taken into account. In contrast to US 2001/0004702 A1, therefore, no breakage and/or impairment of the edge of a blade is to be expected as the blade is guided without its sensitive parts being in contact with the frame, so that according to the invention blades with a greater cutting capability and smaller dimensions may be used.

Especially when penetrating the outer layer of the cornea to prepare a tunnel-like entry, it may thus be assumed that the tunnel-like entry most accurately adjoins the point at which the tip of the blade was previously placed on the cornea. The penetration of the blade is further facilitated by having the holding device support a vibrator for setting the blade in oscillatory motion in the cutting plane. This in particular serves to overcome the elasticity of the outer layer of the cornea without risking an enhanced indentation of the corneal surface. The vibrator also ensures that minimal force is exerted during the cutting process, so that any movement of tissue, which is attributable to the motion of the blade resulting from the elasticity and toughness of the tissue and which tends to arise even when using extremely sharp blades, can be precluded. In comparison to the other state-of-the-art methods, thus a specially drawn cut for high cutting precision may be ensured.

If the receptacle is designed as a receptacle for the stop-delimited receipt of interchangeable applanators with differently curved contact faces intended for applanation of the cornea, said contact faces in sequential incisions defining pockets for delimiting a lens-shaped portion of tissue, it is possible to cut out a portion of tissue via a tunnel-like entry without the need to produce a corneal flap. The lens-shaped portion of tissue which is cut out may subsequently be pulled out via the tunnel-like entry, so that it becomes possible according to the invention to produce a defined cavity in the cornea, thereby insignificantly impairing the stability of the cornea in comparison to the other methods. This allows to create a tissue lens inside the cornea through which a refractive error may be corrected.

If the peripheral edges of the contact faces of the applanators inserted in the receptacle one after another have a different perpendicular distance from the cutting plane of the blade, the cutout of a lens-shaped portion of tissue is thus facilitated. While said difference of the perpendicular distances requires that two tunnel-like entries be produced in the corneal tissue, this has the advantage that the two pockets are prominent in their shared sectional line, which excludes the possibility that the portion of tissue is cut out incompletely.

If the non-metallic blade forms a sharp tip, the blade can penetrate more easily into the tissue from where it is placed on the cornea. If the blade additionally has a sharp edge extending towards the tip, a particularly narrow tunnel-like entry may be produced by radially displacing the blade relative to the fixation ring, which results beneficial for the stability of the cornea.

Particularly advantageous cutting properties of the blade are obtained by designing the blade as a double-edged knife, which is preferably made of diamond material, the blade having a maximum width of 2 mm, a maximum thickness of 200 microns and a blade length of at least 8 mm, preferably 10 mm.

If the applanator is made of transparent material, it becomes easy for the surgeon to monitor the contact face and/or the cutting process. If the applanator is additionally designed as an enlargement lens, the focal point of which lies in the area of the contact face for applanation of the cornea, preferably on the axis of symmetry of the applanator, the monitoring process is even further facilitated.

In order to be able to optimally adjust the size of the contact face of the applanator placed on the eye and/or obtain as exact a cutting area of the pocket as possible, it is recommendable to provide the transparent applanator with markings on its side facing the eye for determining the size of the contact face of the applanator as well as the cutting face on the eye.

If the option of using interchangeable applanators for cutting out a lens-shaped portion of tissue is to be dispensed with, this may be achieved by at least making the applanator contact face of a deformable material, which may then be manipulated by means of an actuator to obtain different curvatures. The actuator thus serves to predefine contact faces with different curvatures for the applanator inserted in the receptacle so as to ensure that a lens-shaped portion of tissue is cut out.

If the blade holder is equipped with a position adjuster operating perpendicular to the cutting plane of the blade, it becomes easy for the surgeon to determine at what depth from the corneal surface to cut the pocket as said position adjuster serves to adjust the distance of the blade from the applanator and/or the contact face of the applanator on the eye.

The blade holder consists, for example, of a lever system comprising at least two lever arms with pivot axes which are perpendicular to the cutting plane of the blade. If one arm receives the blade and the other arm is linked to the frame, this provides a simple construction ensuring that the blade can be radially displaced relative to the fixation ring as well as moved around the axis vertical to its guiding plane.

A further option is for the blade holder to comprise a forked blade guide, which is guided, possibly without clearance, between parallel faces of a peripheral groove provided on the frame, in particular on the receptacle. Not only is this embodiment exceptionally simple in its construction, it also predefines the space within which the surgeon may move the blade.

In order to render the insertion and/or interchange of applanators with their differently curved contact faces as simple as possible, it is suggested that the applanator be held in the receptacle in a stop-delimited position by using a partial vacuum. The only prerequisite for this purpose is to furnish the receptacle with a pressure line which draws out the air between the recess and the applanator.

BRIEF DESCRIPTION OF THE DRAWING

In the drawing the invention is schematically illustrated on the basis of exemplary embodiments.

DESCRIPTION OF THE PREFERRED EMBODIMENT

Figure 1:
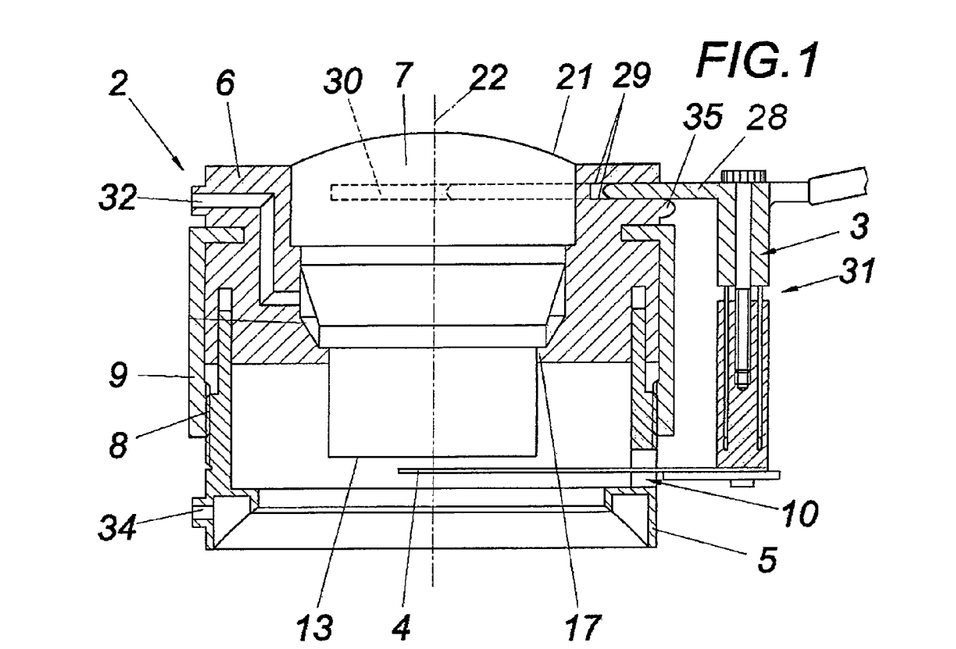
FIG. 1 shows an exemplary embodiment of the device according to the invention in a side view in partial section.
Figure 2:
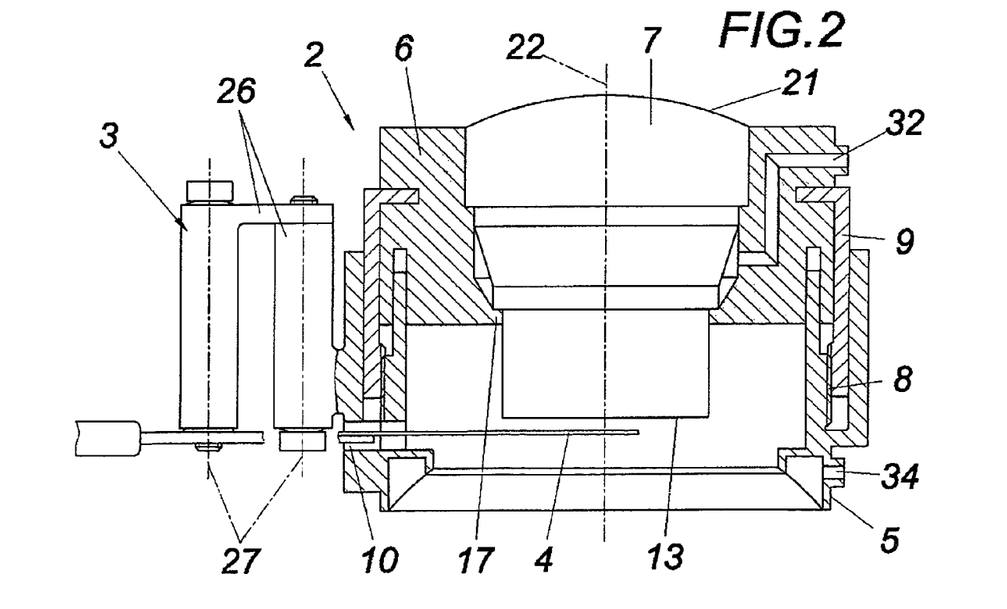
FIG. 2 shows a second exemplary embodiment of the device according to the invention in a side view in partial section.

Pursuant to the exemplary embodiment in FIG. 1 and the exemplary embodiment in FIG. 2, the devices for cutting a cornea 1 of an eye to correct its refractive power according to the invention generally comprise a frame 2 and a holding device 3 for supporting a blade 4. The frame 2 has a fixation ring 5, which may be drawn onto the eye, and a receptacle 6, which may be coaxially displaced relative to the fixation ring 5 and which serves to accommodate an applanator 7 for deforming the cornea within the fixation ring 5. The cornea 1 thus projects through the fixation ring 5, within which, in particular offset in height relative to the fixation ring 5, the applanator 7 for impingement of the cornea is located. The fixation ring 5 is furnished with a thread 8 for coaxial displacement, in which a nut 9 engages that is mounted on the receptacle 6 allowing rotation.

Figure 3A:
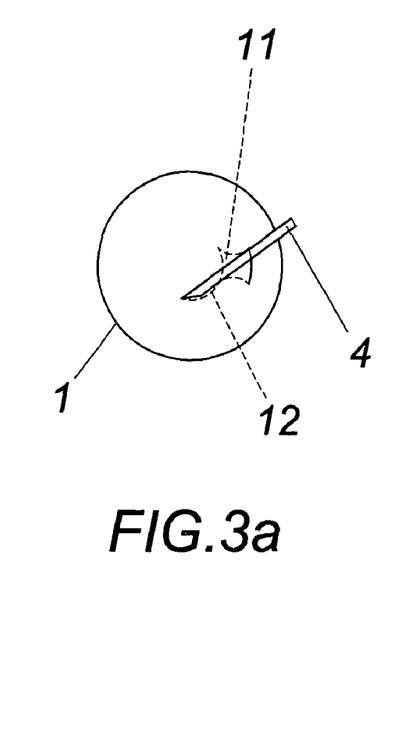
FIG. 3a through c show the direction of the cuts drawn by the blade in the devices illustrated in FIG. 1 or 2 in a top view.
Figure 3B:
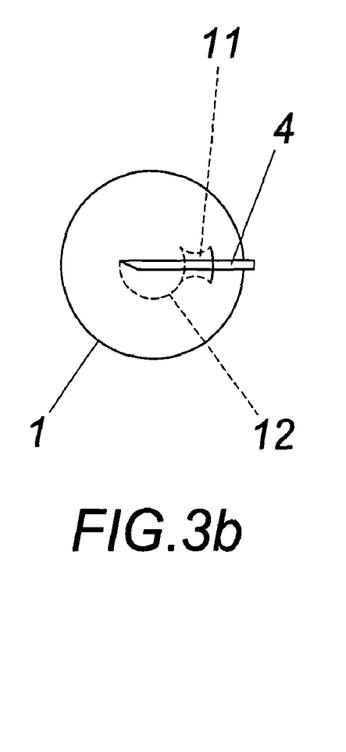
Figure 3C:
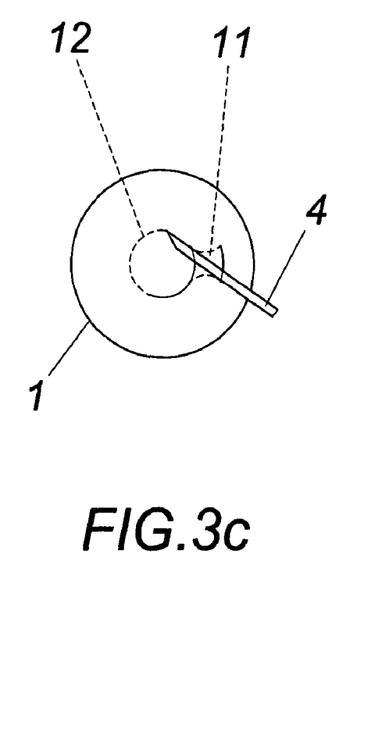
Figure 3D:
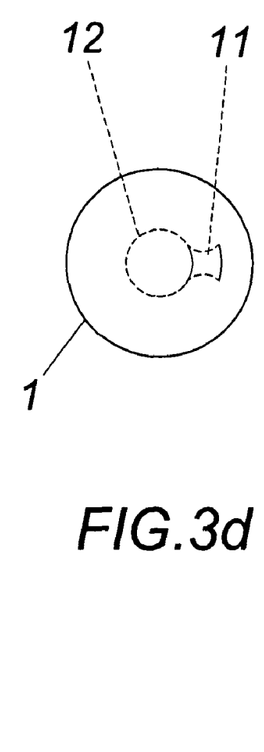
FIG. 3d shows the pocket produced through the cuts performed in FIG. 3a through 3c in a top view.

By rotating the nut 9, the receptacle 6 and/or the applanator 7 may thus be displaced relative to the fixation ring 5 and/or the cornea 1. The holding device 3 for supporting the blade 4 is guided on the frame 2 in a plane that is perpendicular to the axis of the fixation ring 5, and the blade 4 passes through the frame 2 via a peripheral recess 10 with clearance and is mounted in front of the applanator 7. The blade 4 is, in particular, guided by the holding device 3 in such a way that said blade 4 is radially displaceable relative to the fixation ring 5 as well as movable around an axis perpendicular to the guiding plane via the holding device 3, for the purpose of cutting a pocket 12 through a merely tunnel-like entry 11 into the corneal tissue, as may in particular be inferred from FIGS. 3a through 3c.

Figure 4A:
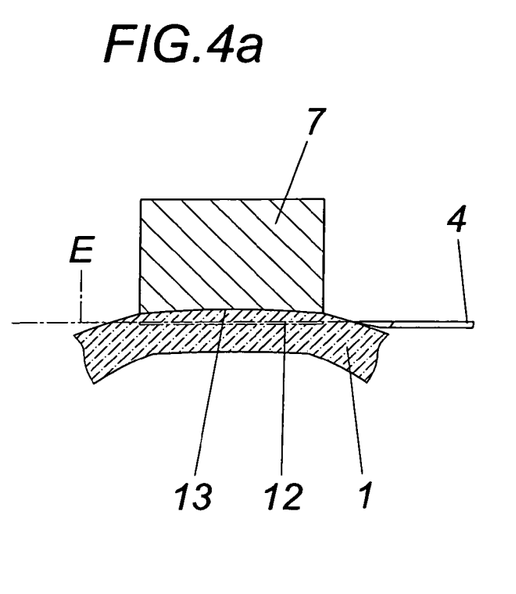
FIG. 4a shows a cornea flattened by applanation with a blade being introduced for producing a pocket in cross section.
Figure 4B:
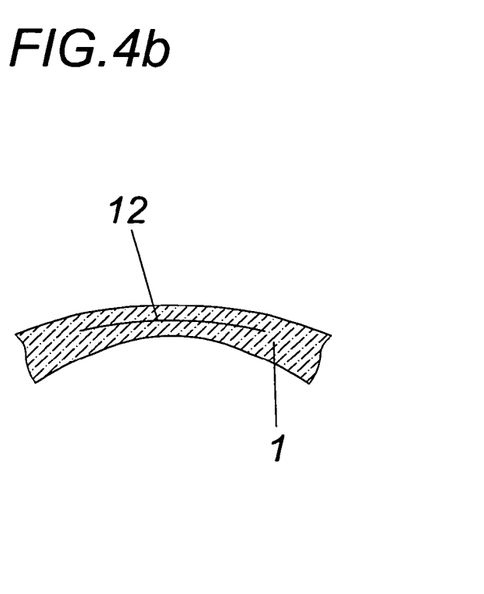
FIG. 4b shows the pocket of an unimpinged cornea produced according to FIG. 4a in cross section.
Figure 5:
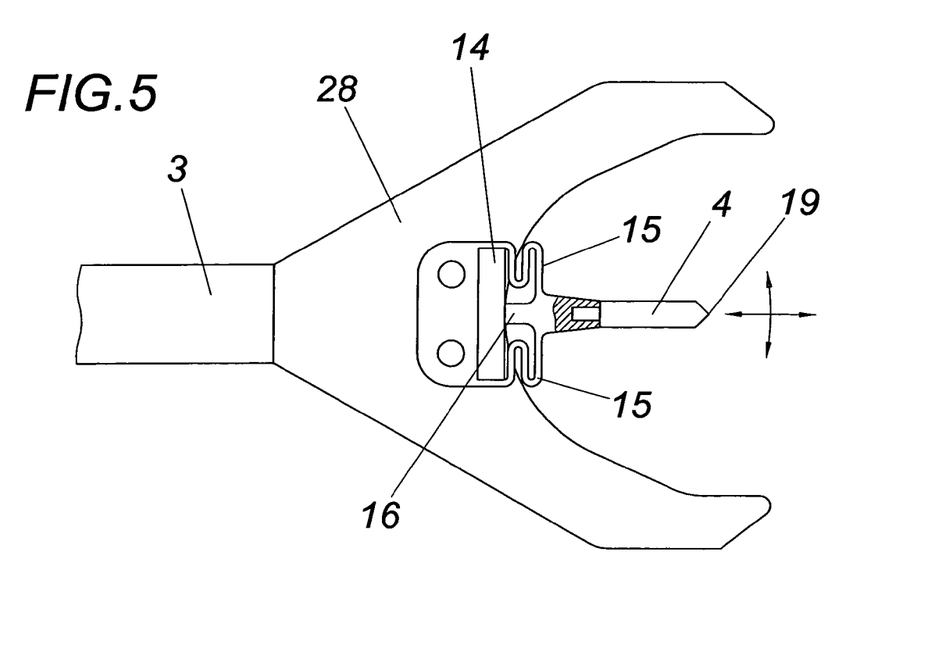
FIG. 5 shows the attachment of the blade to the holding device comprising a forked blade guide.

It is also conceivable that the cutting plane E of the blade 4 also lies in the guiding plane of the blade 4. If a pocket 12 is now to be cut into the cornea 1 (FIG. 4a), an applanator 7 is first pressed onto the corneal surface in such a way that the cornea 1 is deformed in a defined manner corresponding to the contact face 13 of the applanator 7, whereby the shape of the applanator 7 is embossed on the cornea 1. Through said impingement of the cornea 1 a correspondingly large pocket 12 may then be cut into the cornea 1. Once the applanator 7 has been placed on the cornea 1 accordingly, the tip of the blade 4 is placed on cornea 1 and the outer tissue layers of the cornea 1 are penetrated in order to produce a tunnel-like entry 11. It is of decisive importance in this case that the blade 4 does not slip from where it is placed on the corneal surface. The invention therefore comprises a blade 4, which passes through the frame recess 10 with clearance, and the holding device 3 supports a vibrator 14 for setting the blade 4 in oscillatory motion in the cutting plane E, as may be seen in FIG. 5. By passing through the frame recess 10 with clearance, the blade 4 does not rest on the frame as in the other state-of-the-art techniques, so that damage to the blade 4, particularly to the edge of the blade 4, may be precluded. Thus even extremely hard and brittle materials may be used for the blade 4, and because of the resulting sharpness of the blade 4 slipping of the latter as it penetrates into the cornea 1 may virtually be ruled out. However, it has been shown that notwithstanding said blades 4, great force is required to penetrate the outer layer of the cornea 1, which according to the invention is facilitated by an oscillatory motion of the blade 4. For this purpose, the holding device 3 is preferably furnished with a vibrator 14 designed as a piezo element, which vibrates in the cutting plane E of the blade 4. Said vibrator impinges upon the blade 4, which is attached to the holding device 3 by means of springs 15, with the aid of a web 16 pressing against the piezo element. However, using an unbalance motor instead of the piezo element is also conceivable.

Once the tunnel-like entry 11 has been cut through the outer tissue layers of the cornea 1, the blade is guided for the purpose of cutting a pocket 12 in such a way that any further contact with the corneal surface is avoided. Therefore, the pocket 12 produced via the tunnel-like entry 11 is merely cut inside the cornea 1, and it goes without saying that the vibrator 14 further facilitates the cutting process and also allows a highly accurate way of cutting. The pocket 12 and the tunnel-like entry 11 may be adequately widened by using a suitable instrument, whereby the introduction of implants may be facilitated. With the aid of yet another device, an implant which is preferably foldable or deformable may be introduced into the implant bed in the cornea 1 through the tunnel-like orifice 11. The implant then unfolds in the pocket 12 to take on the desired shape.

Since according to the invention a highly exact pocket 12 may be produced inside a cornea 1, it is possible, among other things, to implant lenses which are standardised in terms of their radius of curvature in the area of the optical centre. This is of significance as the natural curvature of the cornea varies between approximately 7 mm and 9 mm and through a flat, uncurved impingement of the cornea 1 a defined radius of curvature of the pocket 12 may not be achieved. By using an applanator 7 with a specifically curved contact face 13 and determining a specific cutting depth, the radius of curvature of the pocket 12 to be produced may be accurately defined. This allows lenses that are standardised in terms of the curvature of their base to be implanted in all patients, which results in significant cost savings in lens manufacturing.

Figure 6A:
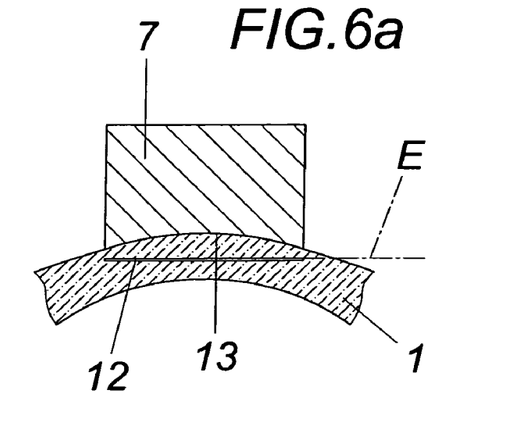
FIG. 6a through c show incisions made to cut out a lens-shaped portion of tissue by using applanators with differently curved contact faces in cross section.
Figure 6B:
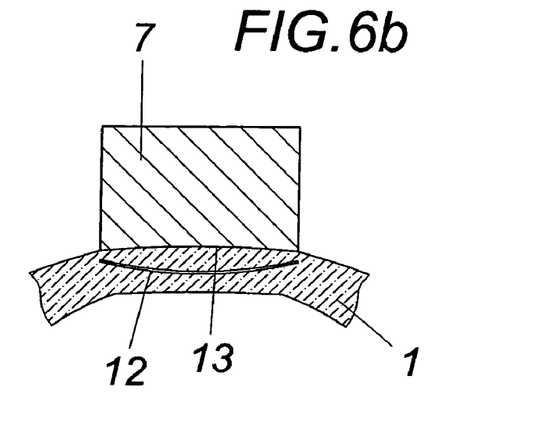
Figure 6C:
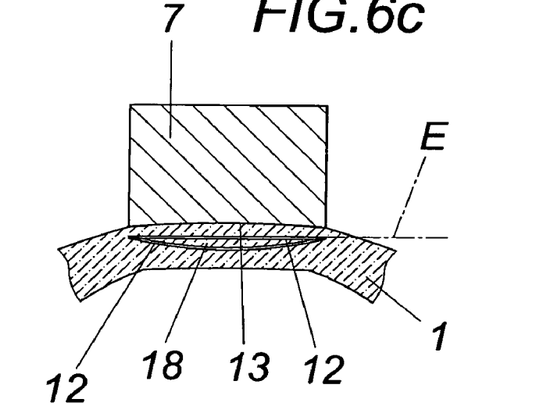

The receptacle 6 accommodating the applanator 7 is designed as a receptacle for the stop-delimited receipt of interchangeable applanators 7 with differently curved contact faces 13 for applanation of the cornea. Said stop 17 is in particular illustrated in FIGS. 1 and 2. This makes it easy to produce pockets 12 for delimiting a lens-shaped portion of tissue 18 by performing sequential incisions. Especially given the fact that the frame 2 need not be withdrawn from the eye while exchanging applanators, the use of a receptacle for interchangeable applanators ensures that always a lens-shaped portion of tissue 18 with a predefined size is cut out, which is not the case if the conventional devices are used. The lens-shaped portion of tissue 18 may be produced according to FIGS. 6a through 6c. After cutting an initial pocket into the corneal tissue, as is also described above, the blade 4 is removed from the corneal tissue (FIG. 6a) and a second pocket 12, embossed by another applanator 7 having a differently curved contact face 13, is incised (FIGS. 6b and c). For this purpose, the applanator 7 either needs to be exchanged or altered with respect to its contact face 13, as may, for example, be achieved using an applanator 7 according to FIG. 7.

By performing a new cut through the tunnel-like entry 11, apart from a new pocket 12 also a lens-shaped portion of tissue 18 (FIG. 6c) is incised, which may be pulled out through the tunnel-like entry 11, for example, by using tweezers. The lens-shaped portion of tissue in its shape corresponds to the difference of the dissimilarly curved contact faces 13 of the two applanators 7 and/or the desired dioptric change through a corresponding alteration of the anterior corneal curvature. The applanator 7 additionally has a grip 36 with an engraved surface in its upper area (FIG. 8e), which makes the applanator 7 easily replaceable. It is useful in this case to ensure that the applanator 7 projects out of the receptacle 6 in order to be grasped easily.

Figure 8A:
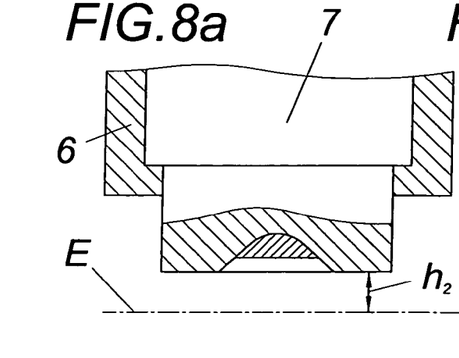
FIG. 8a through g show different applanators for the device according to the invention in a side view.
Figure 8B:
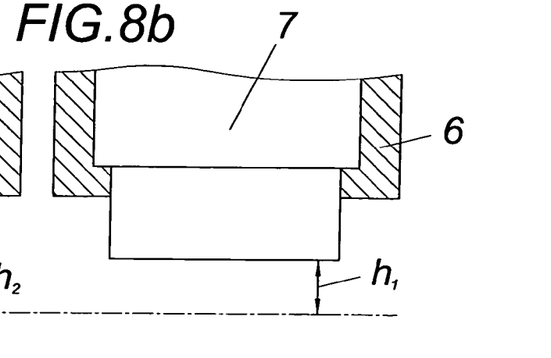
Figure 8C:
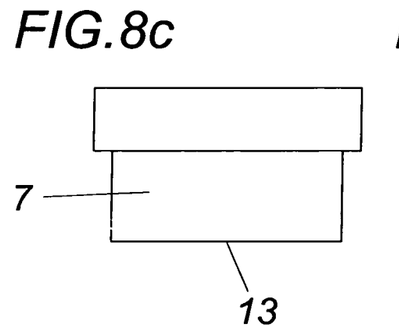
Figure 8D:
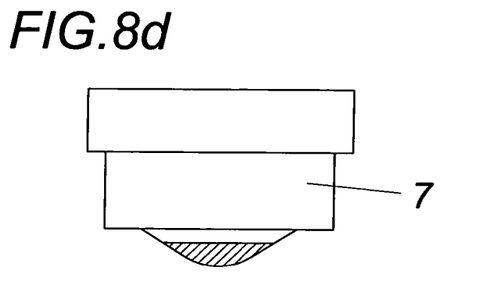
Figure 8E:
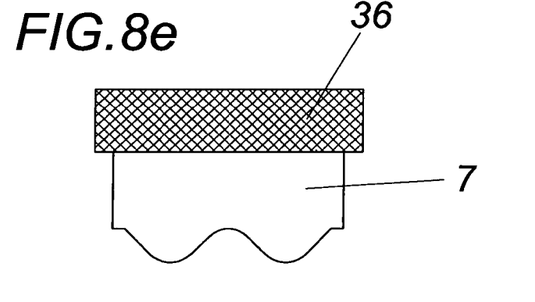
Figure 8F:
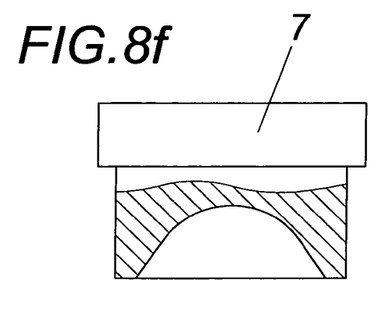
Figure 8G:
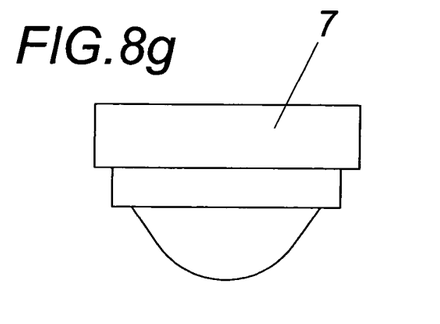

To facilitate the cutout of a lens-shaped portion of tissue 18, the second cut of the blade 4 may be performed somewhat deeper into the cornea 1 (FIGS. 8a and 8b). This may be achieved by ensuring that the perpendicular distances h1 and h2 of the peripheral edges of the contact faces 13 of the applanators 7, which are sequentially inserted in the receptacle 6, are different with respect to the cutting plane E of the blade 4. Exemplary embodiments of different contact faces 13 of applanators 7 are shown in FIG. 8a through g. The dimensions of the lens-shaped portion of tissue 18 that is cut out using the applanators shown in FIGS. 8a and 8b as well as 8c and 8d are indicated by crosshatching.

Figure 9:
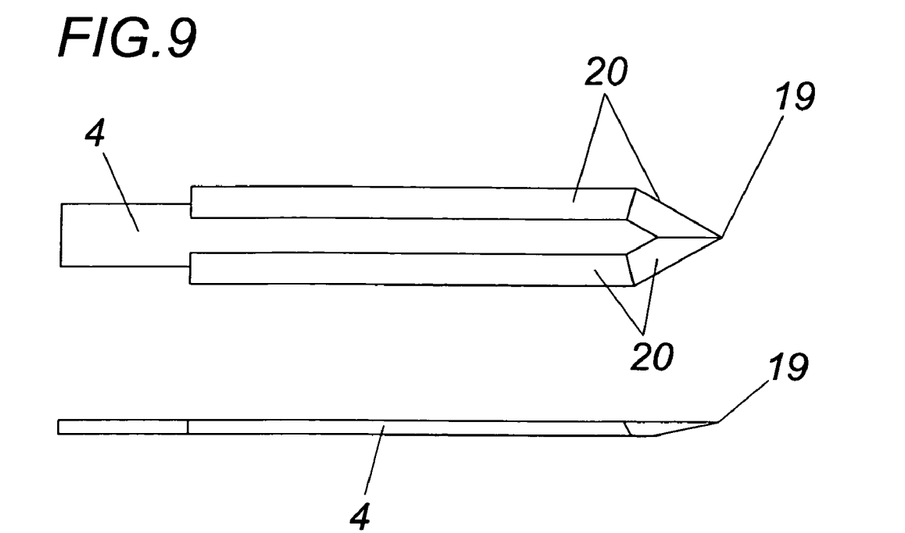
FIG. 9 shows a top and a side view of the blade according to the invention.

The preferably non-metallic blade 4 has a pointed tip 19 with two edges 20 originating from this tip as shown in FIG. 9. This specific type of tip 19 has proven useful for penetrating the outer layer of the cornea 1 and/or producing a tunnel-like entry 11. The shape of the blade 4 resembles that of a double-edged knife. Particularly advantageous cutting properties are obtained if the blade is made of diamond material, having a maximum width of 2 mm, a maximum thickness of 200 microns and a blade length of at least 8 mm, preferably 10 mm.

The applanators 7 are preferably made of transparent material, such as plastic or glass, and are designed as enlargement lenses 21 as illustrated in FIGS. 1 and 2, with their focal point lying in the area of the contact face 13, preferably on the axis of symmetry of the applanator 22. An applanator 7 being designed in such a way makes it relatively easy for a surgeon to monitor the progress of treatment of the cornea 1.

Figure 10:
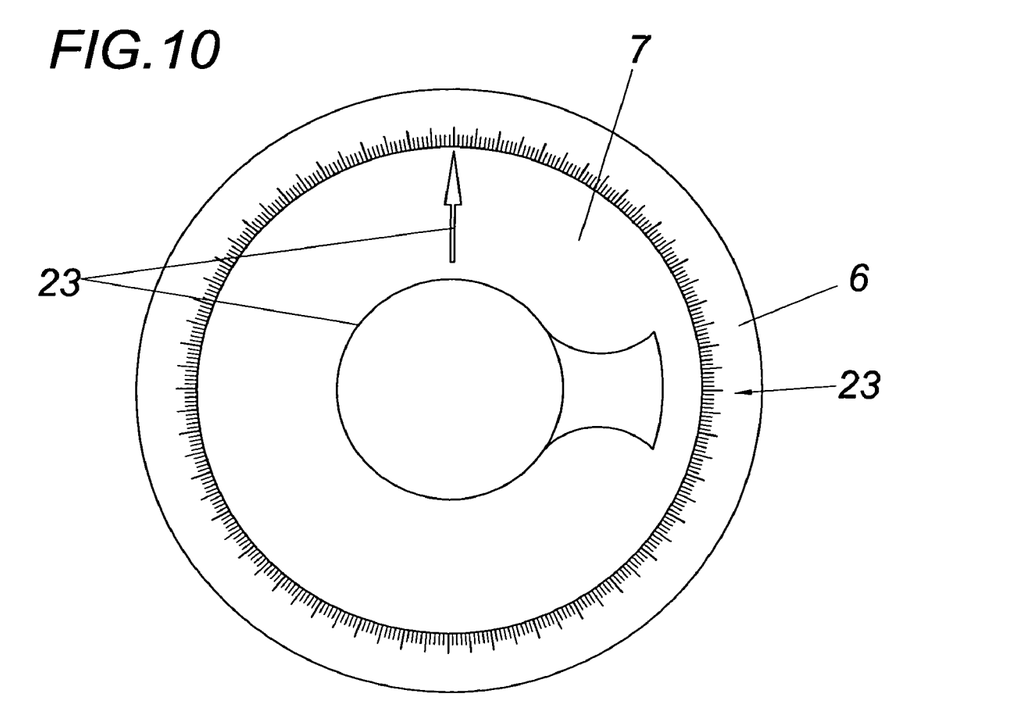
FIG. 10 shows a top view of the device into which a transparent applanator has been inserted.

The transparent applanator 7 has markings 23 on its side facing the eye. These markings 23 enable the surgeon, for example, to optimally orientate himself as to where to introduce the blade 4 for cutting a tunnel-like entry. Markings 23 may also be applied for the optical treatment zone to indicate to the surgeon the boundaries of the pocket 12 to be cut. The transparent applanator 7 also has markings 23 on its side diametrically opposite the eye, which are related to markings 23 on the receptacle 6 for accommodating the applanator 7 (FIG. 10). This enables the surgeon, by offsetting the applanator 7 in relation to the receptacle 6, to perform refractive power corrections, particularly those related to astigmatism.

Figure 7:
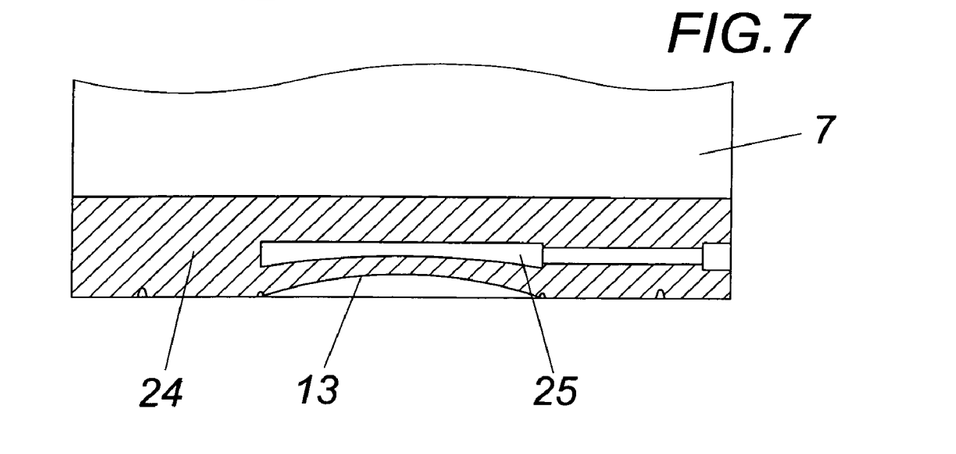
FIG. 7 shows a construction variant of an applanator with a curvable contact face in an enlarged scale.

The contact face 13 of the applanator illustrated in FIG. 7 is made of a deformable material 24, which may be curved via an actuator 25 to obtain different shapes that are maintained. Through a supply line linked to the actuator 25, compressed gas and compressed fluid may be fed into the cavity of the actuator 25, whereby the contact face 13 of the applanator 7 may be curved so as to obtain different shapes that are maintained.

According to the exemplary embodiment illustrated in FIG. 2, the holding device 3 consists of a lever system comprising at least two lever arms 26 having pivot axes 27 which are perpendicular to the cutting plane E of the blade 4; one lever arm 26 receives the blade 4 and the other lever arm 26 is linked to the frame 2, preferably to the receptacle 6.

According to the exemplary embodiment illustrated in FIG. 1, the holding device 3 may also comprise a forked blade guide 28 receiving the blade 4, which is guided, possibly without clearance, between parallel faces 29 of a peripheral groove 30 provided on the frame 2, in particular on the receptacle 6. The blade 4 is offset to the forked blade guide 28, with the distance between the cutting plane E of the blade 4 and the contact face 13 of the applanator 7 being adjustable by means of a position adjuster 31 having the shape of a winding gear. A knob 35 is provided on the receptacle 6 to allow the forked blade guide 28 to be easily pushed in.

The applanator 7 may be fixed into the receptacle 6 by means of a partial vacuum. For this purpose, air may be sucked out of a chamber that is located between the receptacle and the applanator through a line 32. The applanator has the shape of a truncated cone, which allows easy insertion of the applanator. Furthermore, it is conceivable that other mechanical holding devices instead of the pressure line are used, including bayonet closures, magnetic, electromagnetic, hydraulic, or other equivalent mechanisms. A similar procedure is conducted when drawing the fixation ring 5 onto the eye by a pressure line 34.

What is claimed is:

1. A device for cutting a cornea of an eye in order to correct refractive power of the eye comprising:
   (a) a frame comprising a fixation ring drawable onto the eye, a receptacle, and a peripheral recess disposed between the fixation ring and the receptacle;
   (b) an applanator received in the receptacle for deforming the cornea within the fixation ring, said applanator being coaxially displaceable relative to the fixation ring;
   (c) a holding device guided on the frame in a guiding plane perpendicular to an axis of the fixation ring;
   (d) a blade held by the holding device in front of the applanator and passing into the frame through the peripheral recess with a clearance from the frame during cutting into corneal tissue of the cornea, said blade being radially displaceable relative to the fixation ring and movable around an axis perpendicular to the guiding plane via the holding device for cutting into the corneal tissue, the blade not resting on the frame during radial displacement, movement about the axis perpendicular to the guiding plane, and cutting into the corneal tissue; and
   (e) a vibrator supported on the holding device for setting the blade in oscillatory motion in a cutting plane of the blade.

2. The device according to claim 1, wherein said receptacle comprises a changeover receptacle for stop-delimited receipt of interchangeable applanators having differently curved contact faces for applanation of the cornea, the contact faces in sequential incisions determining pockets for delimiting a lens-shaped portion of tissue.

3. The device according to claim 2, wherein said contact faces of the applanators sequentially inserted in the receptacle and the cutting plane of the blade have peripheral edges with different perpendicular distances between the peripheral edges.

4. The device according to claim 2, wherein said applanator is made of transparent material.

5. The device according to claim 4, wherein said applanator has first and second sides, the first side facing the eye having first markings for determining size of the contact face of the applanator on the eye, the second side being averted from the eye having second markings for determining the offset of the applanator in relation to the receptacle.

6. The device according to claim 4, wherein said applanator is designed as an enlargement lens having a focal point lying near the contact face for applanation of the cornea.

7. The device according to claim 2, wherein at least the contact face of the applanator is made of a deformable material curvable via an actuator to obtain different shapes that are maintained.

8. The device according to claim 1, wherein said blade is non-metallic and forms a pointed tip and at least one cutting edge extending towards the tip.

9. The device according to claim 8, wherein said blade is a diamond blade comprising a knife having two edges, the two edges originating from the pointed tip.

10. The device according to claim 9, wherein said blade has a maximum width of 2 mm, a maximum thickness of 200 microns and a blade length of at least 8 mm measured in a penetration direction of the blade.

11. The device according to claim 8 wherein fixation of the blade at the holding device takes place opposite the pointed tip.

12. The device according to claim 1, wherein said holding device has a position adjuster operating perpendicular to the cutting plane of the blade for adjusting the distance of the blade from the applanator.

13. The device according to claim 1, wherein said holding device comprises a lever system comprising at least two lever arms having pivot axes perpendicular to the cutting plane of the blade, one arm receiving the blade and the other arm being linked to the frame.

14. The device according to claim 1, wherein said holding device comprises a forked blade guide for receiving the blade, the forked blade guide being guided free of play with minimal clearance between parallel faces of a peripheral groove provided on the frame.

15. The device according to claim 1, wherein said applanator is held in the receptacle of the frame in a stop-delimited position by using a partial vacuum via a tunnel.

16. The device according to claim 1 wherein said blade is fixed to the holding device at one single position.

17. The device according to claim 1, wherein said blade comprises two cutting edges running parallel along the blade and converging at the distal end of the blade towards a pointed tip.

18. A device for cutting a cornea of an eye in order to correct refractive power of the eye comprising:
   (a) a frame comprising a fixation ring drawable onto the eye, a receptacle, and a peripheral recess disposed between the fixation ring and the receptacle;
   (b) an applanator received in the receptacle for deforming the cornea within the fixation ring, said applanator being coaxially displaceable relative to the fixation ring;
   (c) a holding device mounted on the frame, said holding device comprises a lever system comprising at least a first lever arm and a second lever arm connected via a joint to the first lever arm, each lever arm having a respective pivot axis perpendicular to the cutting plane; and
   (d) a blade held by the holding device in front of the applanator and passing into the frame through the peripheral recess with a clearence from the frame during cutting into corneal tissue of the cornea, said blade being radially displaceable relative to the fixation ring and movable around an axis perpendicular to the guiding plane via the holding device for cutting into the corneal tissue, the blade not resting on the frame during radial displacement, movement about the axis perpendicular to the guiding plane, and cutting into the corneal tissue;
   wherein said holding device further comprises a vibrator which adds an oscillatory motion to the movement of the blade around the pivot axis of the first lever arm.

19. The device according to claim 18, wherein said blade is moveable around the pivot axis of the first lever arm.

20. The device according to claim 18, wherein said blade comprises two cutting edges running parallel along the blade and converging at the distal end of the blade towards a pointed tip.

21. The device according to claim 18, wherein said blade is non metallic.

22. The device according to claim 18, wherein said blade is a diamond blade.

23. The device according to claim 18, wherein the receptacle is designed as a receptacle for the stop-delimited receipt of interchangeable applanators having differently curved contact faces for applanation of the cornea, the contact faces in sequential incisions determining pockets for delimiting a lens-shaped portion of tissue.

* * * * *